United States Patent
Albertorio et al.

(10) Patent No.: US 9,855,064 B2
(45) Date of Patent: Jan. 2, 2018

(54) DRILL GUIDE ASSEMBLY

(71) Applicant: ARTHREX, INC., Naples, FL (US)

(72) Inventors: Ricardo Albertorio, Naples, FL (US); Arley Perez, III, Bonita Springs, FL (US)

(73) Assignee: ARTHREX, INC., Naples, FL (US)

( * ) Notice: Subject to any disclaimer, the term of this patent is extended or adjusted under 35 U.S.C. 154(b) by 920 days.

(21) Appl. No.: 14/088,920

(22) Filed: Nov. 25, 2013

(65) Prior Publication Data
US 2014/0276841 A1    Sep. 18, 2014

Related U.S. Application Data

(60) Provisional application No. 61/782,045, filed on Mar. 14, 2013.

(51) Int. Cl.
*A61B 17/17* (2006.01)
*A61B 17/16* (2006.01)

(52) U.S. Cl.
CPC ........ *A61B 17/175* (2013.01); *A61B 17/1668* (2013.01); *A61B 17/1714* (2013.01); *A61B 17/1721* (2013.01); *A61B 17/1742* (2013.01); *A61B 17/1697* (2013.01); *A61B 17/1703* (2013.01)

(58) Field of Classification Search
CPC . A61B 17/17; A61B 17/1703; A61B 17/1714; A61B 17/1721; A61B 17/1742
See application file for complete search history.

(56) References Cited

U.S. PATENT DOCUMENTS

| | | | | |
|---|---|---|---|---|
| 4,450,835 A | * | 5/1984 | Asnis | A61B 17/1721 606/65 |
| 5,411,504 A | * | 5/1995 | Vilas | A61D 1/00 606/87 |
| 2003/0212405 A1 | | 11/2003 | Choi | |
| 2005/0131546 A1 | | 6/2005 | Mor | |
| 2006/0052795 A1 | * | 3/2006 | White | A61B 17/0401 606/102 |
| 2008/0021479 A1 | | 1/2008 | Penenberg | |

FOREIGN PATENT DOCUMENTS

WO    2011028520 A3    3/2011

OTHER PUBLICATIONS

Extended European Search Report for Application No. EP 14 157 965.6 dated Jun. 16, 2014.
Arthroscopic Reconstructoin of the Ligamentum Teres, by: James M. Simpson, et al., Arthroscopy: The Journal of Arthroscopic and Related Surgery, vol. 27, No. 3 (Mar. 2011); pp. 436-441.

* cited by examiner

*Primary Examiner* — Nicholas Woodall
(74) *Attorney, Agent, or Firm* — Carlson, Gaskey & Olds

(57) ABSTRACT

A drill guide assembly according to an exemplary aspect of the present disclosure includes, among other things, a drill sleeve and an alignment bar spaced from the drill sleeve. A positioning of the drill sleeve is linked to a positioning of the alignment bar.

1 Claim, 6 Drawing Sheets

DRILL GUIDE ASSEMBLY

CROSS REFERENCE TO RELATED APPLICATION

This application claims priority to U.S. Provisional Application No. 61/782,045, which was filed on Mar. 14, 2013.

BACKGROUND

This disclosure relates to orthopedic surgical instrumentation, and more particularly to a drill guide assembly for performing arthroscopic procedures.

Arthroscopic procedures are commonly performed to diagnose and treat problems in joints. For example, ligament reconstruction, bone resurfacing and joint replacement may all be performed using arthroscopic reconstruction procedures that typically require a surgeon to work through a series of portals. In some joints, such as the hip joint, it may be difficult to efficiently and accurately position the surgical instrumentation needed to perform a specific procedure through the arthroscopic portals.

SUMMARY

A drill guide assembly according to an exemplary aspect of the present disclosure includes, among other things, a drill sleeve and an alignment bar spaced from the drill sleeve. A positioning of the drill sleeve is linked to a positioning of the alignment bar.

In a further non-limiting embodiment of the foregoing assembly, the alignment bar extends in parallel with the drill sleeve.

In a further non-limiting embodiment of either of the foregoing assemblies, the drill guide assembly includes a first housing and a second housing spaced from the first housing. The drill sleeve is received through the first housing and the alignment bar is received through the second housing.

In a further non-limiting embodiment of any of the foregoing assemblies, a handle extends from at least one of the first housing and the second housing.

In a further non-limiting embodiment of any of the foregoing assemblies, at least one of the first housing and the second housing includes a mechanism that is actuable to lock a positioning of the drill sleeve or the alignment bar relative to the first housing or the second housing.

In a further non-limiting embodiment of any of the foregoing assemblies, at least one guide pin connects between the first housing and the second housing.

In a further non-limiting embodiment of any of the foregoing assemblies, the drill sleeve is received through a bore formed in the first housing.

In a further non-limiting embodiment of any of the foregoing assemblies, the bore is transverse to an opening formed in the first housing for receiving a guide pin that connects between the first housing and the second housing.

In a further non-limiting embodiment of any of the foregoing assemblies, the alignment bar includes a radiopaque member, and the radiopaque member is visible in a fluoroscopic image of a joint for estimating the positioning of the drill sleeve.

In a further non-limiting embodiment of any of the foregoing assemblies, an instrument is insertable through the drill sleeve to form an opening in a bone.

A surgical method according to another exemplary aspect of the present disclosure includes generating a fluoroscopic image of a joint, positioning an alignment bar of a drill guide assembly at a desired location relative to the joint, visualizing the alignment bar in the fluoroscopic image and selecting a positioning of an instrument to be inserted into the joint based on the positioning of the alignment bar in the fluoroscopic image.

In a further non-limiting embodiment of the foregoing method, the step of generating the fluoroscopic image is performed before the step of positioning the alignment bar.

In a further non-limiting embodiment of either of the foregoing methods, the step of positioning the alignment bar includes adjusting a distance between a first housing and a second housing of the drill guide assembly.

In a further non-limiting embodiment of any of the foregoing methods, the alignment bar is positioned exterior to the joint during the step of positioning.

In a further non-limiting embodiment of any of the foregoing methods, the method includes drilling a tunnel in a bone of the joint after the step of selecting and passing a graft through the tunnel.

A method for reconstructing a ligamentum teres of a hip joint, according to another exemplary aspect of the present disclosure includes, among other things, positioning a drill guide assembly relative to a hip joint, visualizing an alignment bar of the drill guide assembly in an image of the hip joint, adjusting a positioning of a drill sleeve of the drill guide assembly by referencing a positioning of the alignment bar in the image, and reaming a tunnel into a bone of the hip joint through the drill sleeve at the adjusted position.

In a further non-limiting embodiment of the foregoing method, the method includes passing a graft at least partially through the tunnel and fixating the graft with at least one fixation device to reconstruct the ligamentum teres.

In a further non-limiting embodiment of either of the foregoing methods, the method includes the step of fluoroscopically imaging the hip joint prior to the step of positioning the drill guide assembly.

In a further non-limiting embodiment of any of the foregoing methods, the method includes the step of inserting an instrument through the drill sleeve of the drill guide assembly prior to the step of reaming the tunnel.

In a further non-limiting embodiment of any of the foregoing methods, the step of positioning includes aligning the alignment bar in parallel with the drill sleeve.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

Figure 1:
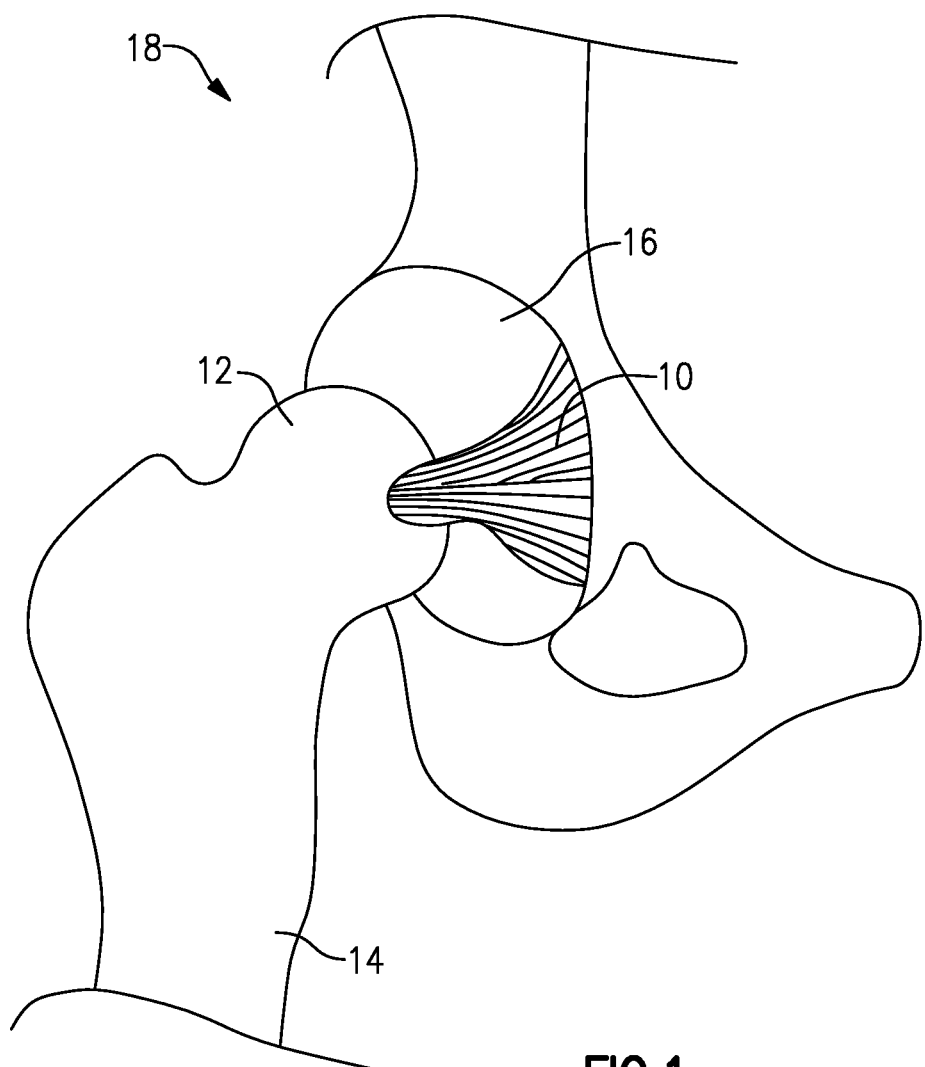
FIG. 1 illustrates a hip joint.

Among other features, this disclosure relates to a surgical device, such as a drill guide assembly, that can be used in various orthopedic procedures to efficiently and accurately position other surgical instrumentation relative to bone. In one non-limiting embodiment, the drill guide assembly of this disclosure is used to prepare a hip joint for reconstructing the ligamentum teres. As shown in FIG. 1, the ligamentum teres 10 connects a femoral head 12 of a femur 14 to an acetabulum 16 of a hip joint 18. Although some embodiments of this disclosure are illustrated in the context of ligamentum teres reconstruction, this disclosure could extend to other orthopedic procedures, including but not limited to, bone resurfacing procedures, joint replacement procedures, or other ligament reconstruction procedures.

Figure 2:
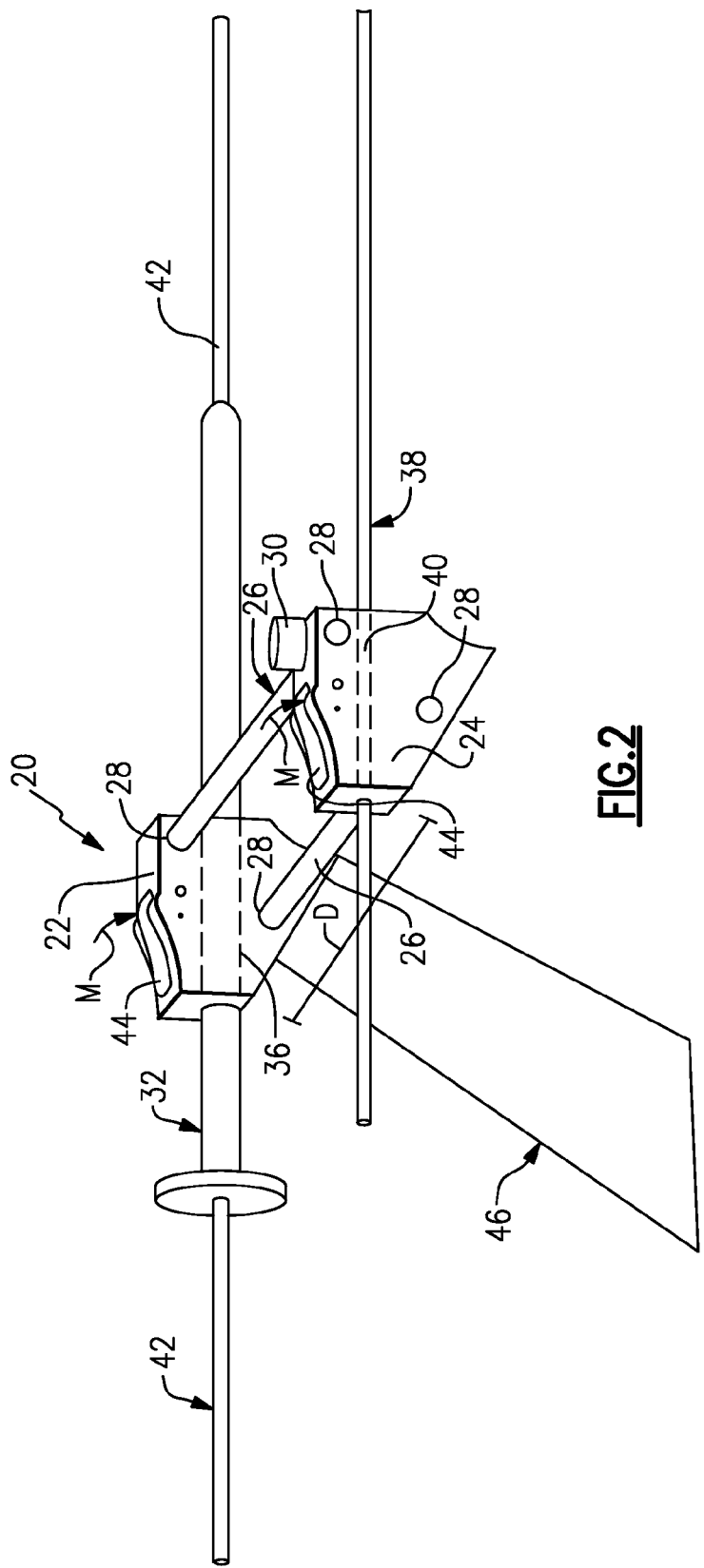
FIG. 2 illustrates an exemplary drill guide assembly.

FIG. 2 illustrates an exemplary drill guide assembly 20. The drill guide assembly 20 is an orthopedic surgical device that may be part of a surgical instrumentation set for preparing a joint for an arthroscopic procedure, such as ligament reconstruction. In one embodiment, the drill guide assembly 20 includes a first housing 22, a second housing 24 and one or more guide pins 26 that connect between the first housing 22 and the second housing 24. In this embodiment, the drill guide assembly 20 includes two guide pins 26. However, a greater or fewer number of pins may extend between the first and second housings 22, 24 within the scope of this disclosure. The guide pins 26 may be received in openings 28 that extend through each of the first housing 22 and the second housing 24.

The first housing 22 and the second housing 24 may be positioned in a parallel relationship relative to one another. In one embodiment, the first housing 22 and the second housing 24 are movable along the guide pins 26 to adjust a distance D that extends between the first housing 22 and the second housing 24. The distance D that extends between the first housing 22 and the second housing 24 may depend on the size of the joint the drill guide assembly 20 is to be positioned relative to, among other surgical criteria. The drill guide assembly 20 may additionally include a locking pin 30 that adjustably locks a positioning of the first and second housings 22, 24 relative to one another. The locking pin 30 could be disposed on the first housing 22, the second housing 24, or both, and can be turned to lock/unlock movement of the first housing 22 and/or the second housing 24 along the guide pins 26.

In one embodiment, a drill sleeve 32 is received through a bore 36 of the first housing 22 and an alignment bar 38 is received through a bore 40 of the second housing 24. The bores 36, 40 are transverse to the openings 28, in this embodiment. The drill sleeve 32 and the alignment bar 38 are generally parallel to one another such that the alignment bar 38 can be used to accurately position the drill sleeve 32. In other words, the positioning of the drill sleeve 32 is linked to the positioning of the alignment bar 38.

For example, the alignment bar 38 is a radiopaque member and can include a metallic rod or other structure that is visible in fluoroscopic images. Therefore, the alignment bar 38 can be relied on to estimate the positioning of an instrument 42 inserted through the drill sleeve 32 and into the joint space. For example, the instrument 42, such as a guide pin or drill, can be inserted through the drill sleeve 32 to create a bone tunnel that may be needed to prepare a joint for an arthroscopic procedure.

The drill sleeve 32 and the alignment bar 38 are axially adjustable relative to the first housing 22 and the second housing 24, respectively. Each housing 22, 24 includes a mechanism 44 that can be actuated in an inward pivoting motion M to permit or prevent movement of the drill sleeve 32 and alignment bar 38 within the bores 36, 40.

A handle 46 may extend from at least one of the first housing 22 and the second housing 24 (or both). The handle 46 allows a surgeon to grip the drill guide assembly 20 when positioning it relative to a joint or bone. In this embodiment, the handle 46 extends from the first housing 22 at a transverse angle relative to the drill sleeve 32. The size, shape and other design characteristics of the handle 46 are not intended to limit this disclosure.

FIGS. 3, 4, 5A, 5B, 6, 7 and 8 schematically illustrate an exemplary method for performing an arthroscopic procedure using the drill guide assembly 20 described above and illustrated in FIG. 2. The exemplary drill guide assembly 20 efficiently and accurately positions surgical instrumentation needed to perform a specific arthroscopic procedure. In this embodiment, the method includes the reconstruction of a ligamentum teres of the hip joint. However, this disclosure is not limited to the reconstruction of the ligamentum teres. In addition, the method could include greater or fewer method steps and these steps could be performed in a different order than described herein within the scope of this disclosure.

Figure 3:
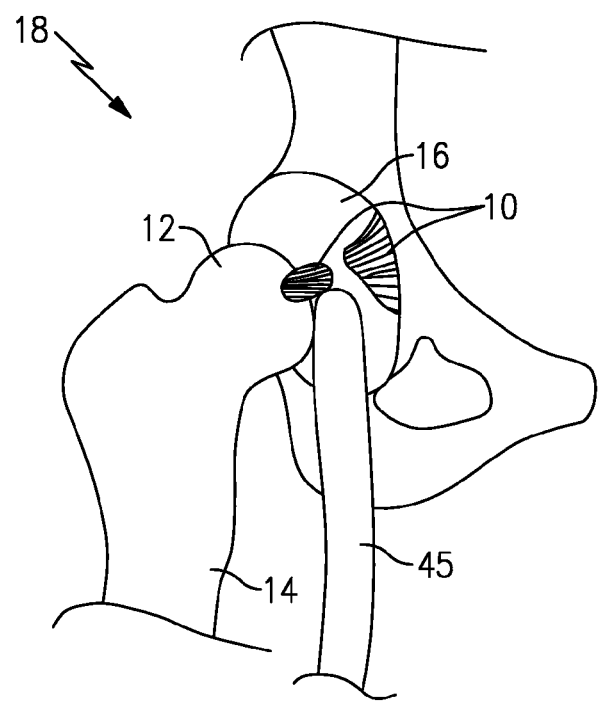
FIG. 3 schematically illustrates a portion of an exemplary method for performing an arthroscopic procedure, such as a ligamentum teres reconstruction.

In one non-limiting embodiment, as illustrated by FIG. 3, the method begins by preparing the hip joint 18 for the arthroscopic surgical procedure. If necessary, the entire ligamentum teres 10 may be resected using a resection device 45 (shown schematically), such as a shaver. Additional procedures may also be performed to prepare the hip joint 18 for the arthroscopic procedure, such as preparing a bleeding bone bed with a rasp, etc.

Figure 4:
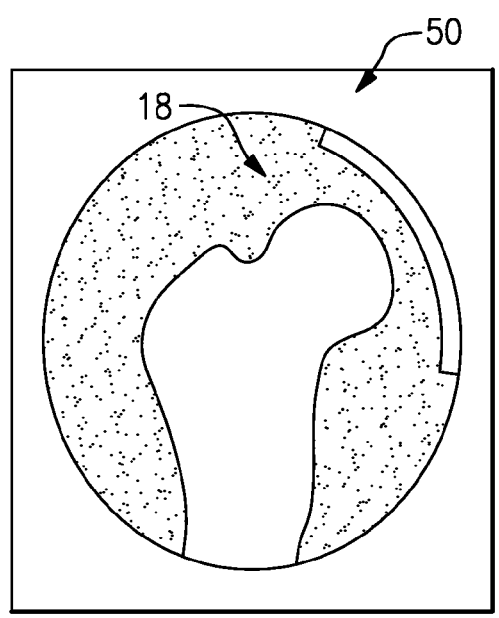
FIG. 4 illustrates a fluoroscopic image of a joint.

FIG. 4 illustrates a fluoroscopic image 50 of the hip joint 18 that can be generated either before or after the step of preparing the hip joint 18 by resecting the ligamentum teres 10. The fluoroscopic image 50 provides real-time, moving images of the internal structure of a patient through the use of a fluoroscope. A person of ordinary skill in the art would understand how to generate a fluoroscopic image of a joint using a fluoroscope.

Figure 5A:
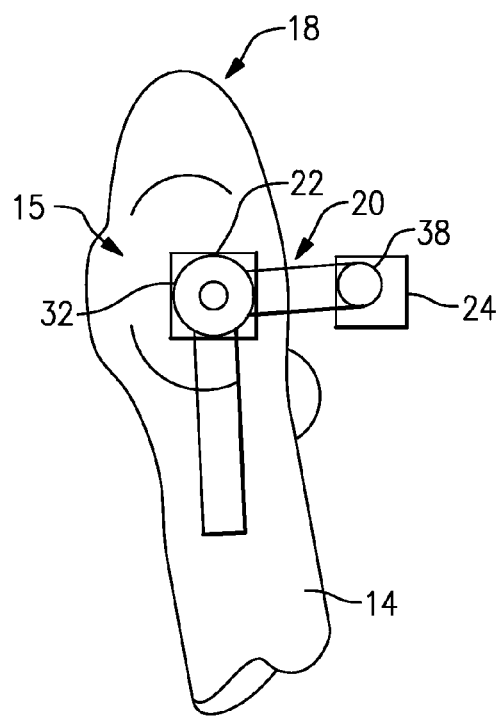
FIGS. 5A and 5B illustrate the positioning of a drill guide assembly for use in performing an arthroscopic procedure.
Figure 5B:
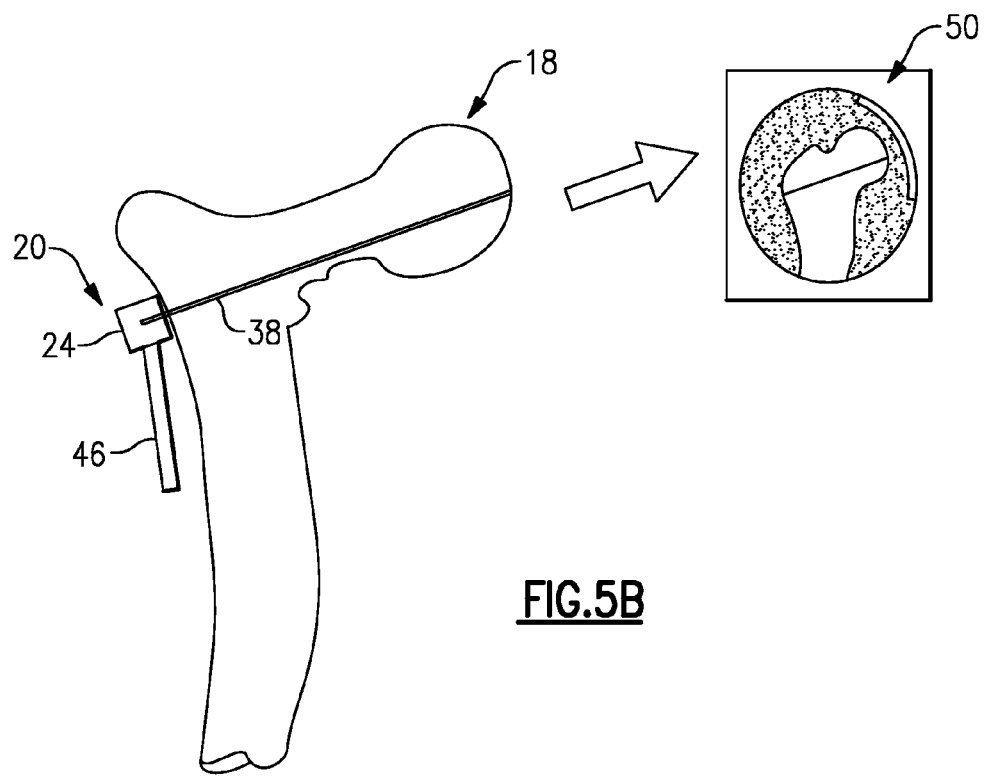

Referring to FIGS. 5A and 5B, the drill guide assembly 20 may next be positioned relative to the hip joint 18. FIG. 5A illustrates a lateral view of the femur 14, and FIG. 5B illustrates an anterior/posterior view of the hip joint 18. The first housing 22 of the drill guide assembly 20 may be aligned with the center of a femoral neck 15 of the femur 14, and the alignment bar 38 of the drill guide assembly 20 may be positioned outside the skin of the patient in the vicinity of the hip joint 18 (i.e., exterior to the joint). The distance D (see FIG. 2) between the first housing 22 and the second housing 24 can be adjusted to position the alignment bar 38 at a desired location relative to the hip joint 18. The alignment bar 38 is visible in the fluoroscopic image 50 due to its radiopaque nature. Because the alignment bar 38 is maintained in parallel with the drill sleeve 32, the alignment bar 38 shows the lateral to medial trajectory of the drill sleeve 32. The positioning of the alignment bar 38 can be adjusted by adjusting the distance D as well as axially moving the alignment bar 38 and drill sleeve 32 relative to the housings 22, 24 by actuating the mechanisms 44 (see FIG. 2).

Figure 6:
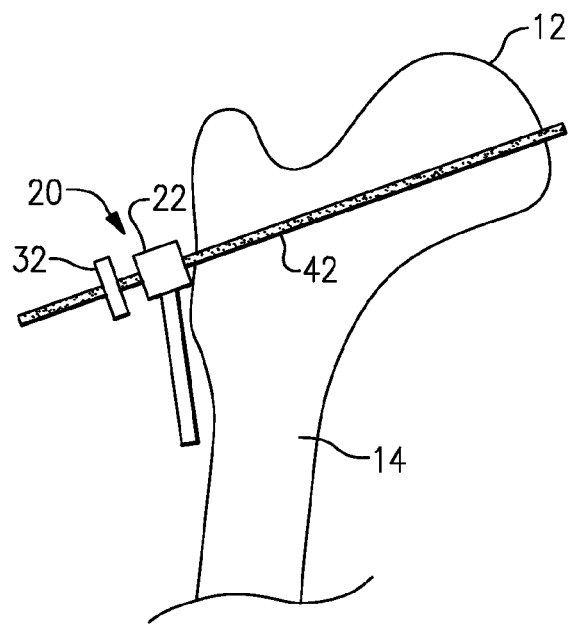
FIGS. 6, 7, and 8 illustrate additional steps of an exemplary method for performing an arthroscopic procedure.

Once the surgeon is satisfied with a positioning of the alignment bar in the fluoroscopic image 50 of the hip joint 18, an instrument 42, such as a guide pin, can be inserted through the drill sleeve 32 into the femur 14 (see FIG. 6). In this embodiment, the instrument 42 is driven from the lateral aspect of the femur 14 and through a femoral head 12 of the femur 14 until the instrument exits through the femoral head 12. The ideal exiting location of the instrument 42 is the native location of the ligamentum teres 10 (i.e., the location where the ligamentum teres connects to the femoral head 12). The drill guide assembly 20 may be removed once the surgeon is satisfied with the exiting location of the instrument 42.

Figure 7:
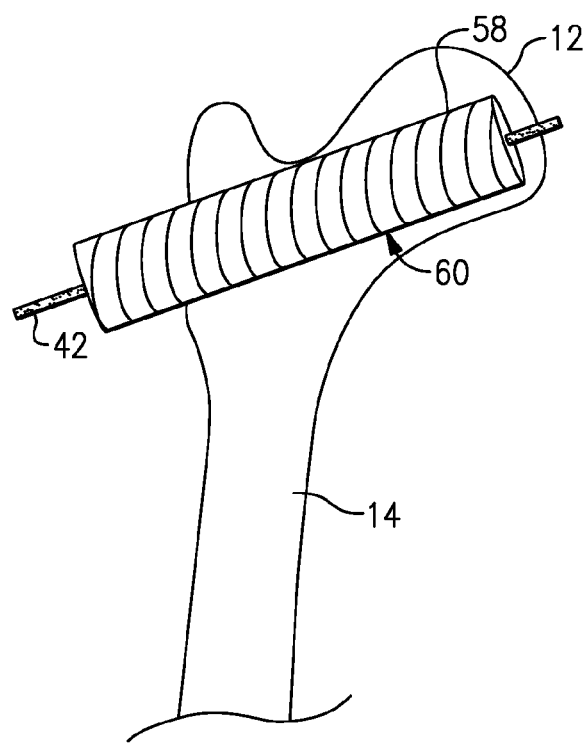

A cannulated drill bit 58 is next placed over the instrument 42 to ream a bone tunnel 60 into the femur 14. This is illustrated in FIG. 7. The size of the instrument 42 and the cannulated drill bit 58 may vary depending upon the size of the patient and the size of the graft that is to be passed, among other criteria. Once the bone tunnel 60 is formed, the cannulated drill bit 58 and the instrument 42 may be removed from the hip joint 18. The acetabulum 16 of the hip joint 18 may then be prepared for acetabular fixation through a variety of arthroscopic portals (not shown).

Figure 8:
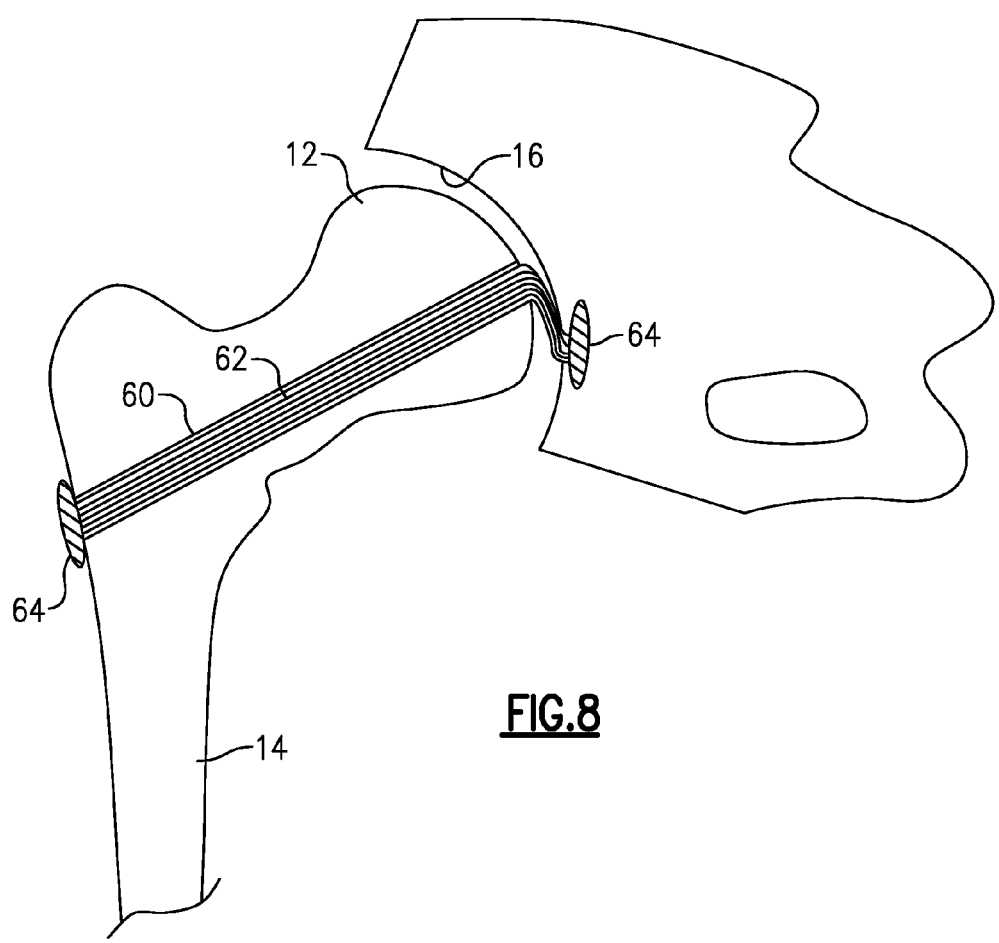

Finally, as shown in FIG. 8, a graft 62 can be passed through the bone tunnel 60 to complete the ligamentum teres reconstruction. The hip joint 18 may need abducted prior to passing the graft 60. The graft 62 may be any type of graft, including an artificial or natural graft. Acetabular fixation and femoral fixation of the graft 62 may be achieved using a fixation device 64, such as a barbed post, a screw, or a suspensory fixation device. Arthrex's Retrobutton® and ACL Tightrope® are non-limiting examples of fixation devices that may be used to achieve graft fixation. One fixation location of the acetabular component of the reconstruction is on the inner lamina of the pelvis, whereas the femoral fixation can be located at the lateral aspect of the femur 14.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical method, comprising:
    generating a fluoroscopic image of a joint;
    resecting a ligament either before or after the step of generating the fluoroscopic image;
    positioning an alignment bar of a drill guide assembly at a desired location relative to the joint, the drill guide assembly including a first housing, a second housing spaced from and movable relative to the first housing, a drill sleeve received through the first housing, and the alignment bar is received through the second housing, wherein a positioning of the drill sleeve is linked to a positioning of the alignment bar such that the alignment bar is maintained in parallel with the drill sleeve as the second housing is moved relative to the first housing;
    visualizing the alignment bar in the fluoroscopic image; and
    selecting a positioning of an instrument to be inserted into the joint based on the positioning of the alignment bar in the fluoroscopic image.

* * * * *